United States Patent [19]

Maurer et al.

[11] 4,219,546
[45] Aug. 26, 1980

[54] COMBATING ARTHROPODS WITH O,O-DIALKYL-O-[1-ISOPROPYL-1,6-DIHYDRO-6-OXO-PYRIDAZIN-3-YL]-PHOSPHORIC ACID ESTERS

[75] Inventors: Fritz Maurer, Wuppertal; Ingeborg Hammann, Cologne, both of Fed. Rep. of Germany

[73] Assignee: Bayer Atkiengesellschaft, Leverkusen, Fed. Rep. of Germany

[21] Appl. No.: 920,506

[22] Filed: Jun. 29, 1978

[30] Foreign Application Priority Data

Jul. 15, 1977 [DE] Fed. Rep. of Germany ....... 2732101

[51] Int. Cl.² ............................ C07F 9/65; A01N 9/36
[52] U.S. Cl. ..................................... 424/200; 544/232
[58] Field of Search .......................... 424/200; 544/232

[56] References Cited

U.S. PATENT DOCUMENTS

| | | | |
|---|---|---|---|
| 2,759,937 | 8/1956 | Du Breuil | 544/232 |
| 3,100,206 | 8/1963 | Rigterink | 544/232 |
| 3,544,572 | 12/1970 | Fest et al. | 544/232 |
| 4,013,657 | 3/1977 | Hofer et al. | 544/232 |
| 4,058,603 | 11/1977 | Hofer et al. | 544/232 |

OTHER PUBLICATIONS

Du Breuil II, J. Org. Chem 26, 3382 (1961).

*Primary Examiner*—Mark L. Berch
*Attorney, Agent, or Firm*—Sprung, Felfe, Horn, Lynch & Kramer

[57] ABSTRACT

O,O-Dialkyl-O-[1-isopropyl-1,6-dihydro-6-oxo-pyridazin-3-yl]-phosphoric acid esters of the formula

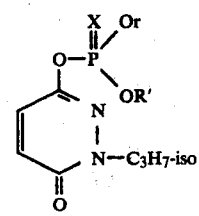

wherein
R and R' each independently is alkyl with 1 to 8 carbon atoms, and
X is oxygen or sulphur which possess arthropodicidal properties.

10 Claims, No Drawings

COMBATING ARTHROPODS WITH O,O-DIALKYL-O-[1-ISOPROPYL-1,6-DIHYDRO-6-OXO-PYRIDAZIN-3-YL]-PHOSPHORIC ACID ESTERS

The present invention relates to and has for its objects the provision of particular new O,O-dialkyl-O-[1-isopropyl-1,6-dihydro-6-oxo-pyridazin-3-yl]-phosphoric acid esters which possess arthropodicidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is already known that certain O,O-dialkyl-O-pyridazinyl-thionophosphoric acid esters, for example O,O-diethyl-O-(1-phenyl-1,6-dihydro-pyridaz-6-on-3-yl)-thionophosphoric acid ester, are distinguished by an insecticidal and acaricidal activity (see U.S. Pat. No. 2,759,937).

The present invention now provides, as new compounds, the pyridazinone(thiono)-phosphoric acid esters of the general formula

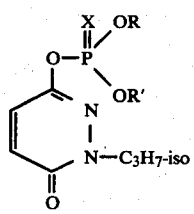
(I)

wherein
R and R', which may be identical or different, each represent alkyl and
X represents oxygen or sulphur.

These new compounds are distinguished by powerful insecticidal and acaricidal properties.

Preferably, R and R', which may be identical or different, each represent straight-chain or branched alkyl with 1 to 8 (especially 1 to 4) carbon atoms and X represents sulphur.

The present invention also provides a process for the preparation of a pyridazinone(thiono)-phosphoric acid ester of the formula (I), in which a (thiono)phosphoric acid diester halide of the general formula

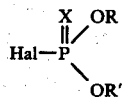
(II)

in which
R, R' and X have the above-mentioned meanings and
Hal represents halogen, preferably chlorine,
is reacted, if appropriate in the presence of a diluent or solvent, with 1,6-dihydro-3-hydroxy-1-isopropyl-pyridazin-6-one of the formula

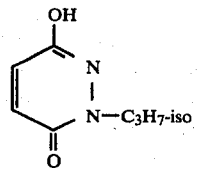
(III)

the latter being employed as such, in the presence of an acid acceptor, or in the form of an alkali metal salt, alkaline earth metal salt or ammonium salt.

Surprisingly, the pyridazinone(thiono)-phosphoric acid esters (I) according to the invention exhibit a better insecticidal and acaricidal action than the previously known compounds of analogous structure and of the same type of action. The products according to the present invention thus represent a genuine enrichment of the art.

If, for example, O-ethyl-O-sec.-butyl-phosphoric acid diester chloride and 1,6-dihydro-3-hydroxy-1-isopropylpyridazin-6-one are used as starting materials, the course of the reaction can be represented by the following equation:

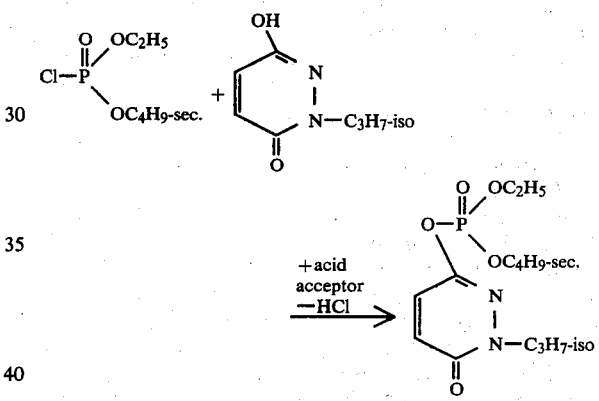

The (thiono)phosphoric acid diester halides (II) to be used as starting materials are known and can readily be prepared, even industrially, in accordance with processes known from the literature. As specific examples of these compounds, there may be mentioned: O,O-dimethyl-, O,O-diethyl-, O,O-di-n-propyl-, O,O-di-isopropyl-, O,O-di-n-butyl-, O,O-di-iso-butyl-, O,O-di-sec.-butyl-, O-methyl-O-ethyl-, O-methyl-O-n-propyl-, O-methyl-O-iso-propyl-, O-methyl-O-n-butyl-, O-methyl-O-iso-butyl-, O-methyl-O-sec.-butyl-, O-ethyl-O-n-propyl-, O-ethyl-O-iso-propyl-, O-ethyl-O-n-butyl-, O-ethyl-O-iso-butyl-, O-ethyl-O-sec.-butyl-, O-n-propyl-O-iso-propyl-, O-n-propyl-O-n-butyl-, O-n-propyl-O-iso-butyl-, O-n-propyl-O-sec.-butyl-, O-iso-propyl-O-n-butyl-, O-iso-propyl-O-iso-butyl- and O-iso-propyl-O-sec.-butylphosphoric acid diester chloride and the corresponding thiono analogues.

1,6-Dihydro-3-hydroxy-1-isopropyl-pyridazin-6-one (III), also to be used as a starting material, can also be prepared in accordance with processes known from the literature.

The process for the preparation of the compounds according to the invention is preferably carried out in the presence of a suitable solvent or diluent. Virtually all inert organic solvents can be used for this purpose, especially aliphatic and aromatic, optionally chlorinated hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example trimethylamine, triethylamine, dimethylaniline, dimethylbenzylamine and pyridine.

The reaction temperature can be varied within a substantial range. In general, the reaction is carried out at from 0° to 100° C., preferably at from 20° to 60° C.

In general, the reaction is allowed to take place under normal pressure.

To carry out the process, the starting components are preferably employed in equimolar amounts. An excess of one or the other component produces no significant advantages. In general, the reactants are brought together in one of the stated solvents and are stirred, in most cases at an elevated temperature, for from one to several hours, in order to complete the reaction. Thereafter, an organic solvent, for example toluene, is added and the organic phase is worked up in the usual manner by washing, drying and distilling off the solvent.

The new compounds are obtained in the form of oils which in most cases cannot be distilled without decomposition but are freed from the last volatile constituents by so-called "incipient distillation", that is to say by prolonged heating under reduced pressure to moderately elevated temperatures, and are purified in this manner. They are characterized by the refractive index.

As already mentioned, the compounds according to the present invention are distinguished by an excellent insecticidal and acaricidal activity. They are therefore active against plant pests, pests harmful to health and pests of stored products and combine a low phytotoxicity with a good action against sucking and biting insects and against mites.

For this reason, the compounds according to the invention can be employed successfully as pesticides in plant protection and in the hygiene field and the field of protection of stored products.

The compounds according to the present invention can also be used in the field of verterinary medicine since they are also active against animal parasites, in particular ectoparasites such as parasitic fly larvae.

The active compounds are well tolerated by plants, have a favorable level of toxicity to warm-blooded animals, and can be used for combating arthropod pests, especially insects and acarids, which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera* spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria;* from the order of the Dermaptera, for example *Forficula auricularia;* from the order of the Isoptera, for example *Reticulitermes* spp.;

from the order of the Anoplura, for example *Phylloxera vastatrix, Pemphigus* spp., *Pediculus humanus corporis, Haematopinus* spp. and *Linognathus* spp.;

from the order of the Mallophaga, for example *Trichodectes* spp. and *Damalinea* spp.;

from the order of the Thysanoptera, for example *Hercinothrips femoralis* and *Thrips tabaci;* from the order of the Heteroptera, for example *Eurygaster* spp., *Dysdercus intermedius, Piesma quadrata, Cimex lectularius, Rhodnius prolixus* and *Triatoma* spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis* and *Costelytra zealandica;* from the order of the Hymenoptera, for example *Diprion* spp., *Hoplocampa* spp., *Lasius* spp., *Monomorium pharaonis* and *Vespa* spp.;

from the order of the Diptera, for example *Aedes* spp., *Anopheles* spp., *Culex* spp., *Drosophila melanogaster,*

*Musca* spp., *Fannia* spp., *Calliphora erythrocephala*, *Lucilia* spp., *Chrysomyia* spp., *Cuterebra* spp., *Gastrophilus* spp., *Hyppobosca* spp., *Stomoxys* spp., *Cestrus* spp., *Hypoderma* spp., *Tabanus* spp., *Tannia* spp., *Bibio hortulanus*, *Oscinella frit*, *Phorbia* spp., *Pegomyia hyoscyami*, *Ceratitis capitata*, *Dacus oleae* and *Tipula paludosa*;

from the order of the Siphonaptera, for example *Xenopsylla cheopis* and *Ceratophyllus* spp.;

from the order of the Acarina, for example *Acarus siro*, *Argas* spp., *Ornithodoros* spp., *Dermanyssus gallinae*, *Eriophyes ribis*, *Phyllocoptruta oleivora*, *Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa*, *Panonychus* spp. and *Tetranychus* spp.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexanes or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The present invention also provides an arthropodicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects and acarids) which comprises applying to the arthropods, or to a habitat thereof, a compound of the present invention alone or in the form of a composition containing as active ingredient a compound of the present invention in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

The following example illustrates the preparation of the novel compounds:

a) 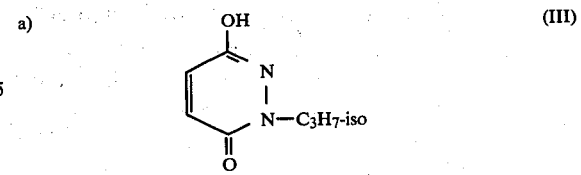 (III)

58.8 g (0.6 mol) of maleic anhydride were added to a solution of 73.8 g (0.6 mol) of isopropylhydrazine sulphate in 180 ml of water and 10 ml of concentrated hydrochloric acid at 60° C. The mixture was then boiled for 3 hours under reflux after which it was cooled to 0° C. After half an hour, the product which had precipitated was filtered off. 59 g (64% of theory) of 1-isopropyl-1,6-dihydro-3-hydroxy-6-oxo-pyridazine were thus obtained in the form of colorless crystals of melting point 148° C.

b)

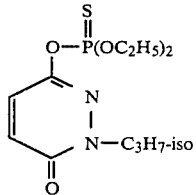

(1)

A mixture of 15.4 g (0.1 mol) of 1-isopropyl-1,6-dihydro-3-hydroxy-6-oxo-pyridazine, 20.7 g (0.15 mol) of potassium carbonate, 300 ml of acetonitrile and 18.9 g (0.1 mol) of O,O-diethylthionophosphoric acid diester chloride was stirred for 5 hours at 45° C. 400 ml of toluene were then added and the reaction mixture was extracted by shaking twice with 300 ml of water. The organic phase was dried over sodium sulphate and the solvent was then distilled off in vacuo. The residue was subjected to incipient distillation at about 80° C. In this way, 25.3 g (76% of theory) of O,O-diethyl-O-[1-isopropyl-1,6-dihydro-6-oxo-pyridazin-3-yl]-thionophosphoric acid ester were obtained in the form of a light brown oil having a refractive index $n_D^{23}$ of 1.5078.

The following compounds of the formula

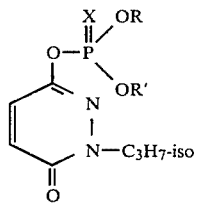

(I)

could be prepared analogously:

Table 1

| Compound No. | R | R' | X | Yield (% of theory) | Refractive index: |
|---|---|---|---|---|---|
| 2 | CH$_3$ | CH$_3$ | S | 71 | $n_D^{23}$:1.5220 |
| 3 | C$_2$H$_5$ | C$_2$H$_5$ | O | 85 | $n_D^{21}$:1.4856 |
| 4 | CH$_3$ | C$_3$H$_7$-n | S | 78 | $n_D^{21}$:1.5099 |
| 5 | C$_2$H$_5$ | C$_3$H$_7$-n | S | 85 | $n_D^{21}$:1.5043 |
| 6 | CH$_3$ | C$_2$H$_5$ | S | | |

The insecticidal and acaricidal activity of the compounds of this invention is illustrated by the following examples wherein the compounds according to the present invention are each identified by the number (given in brackets) from Example 1.

The known comparison compound is identified as follows:

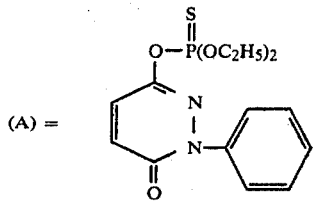

(A) =

EXAMPLE 2

Myzus test (contact action)

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% meant that all of the aphids were killed whereas 0% meant that none of the aphids were killed.

The active compounds, the concentrations of the active compounds, the evaluation times and the results can be seen from the following table:

TABLE 2

| | (insects which damage plants) Myzus Test | |
|---|---|---|
| Active compounds | Active compound concentration in % | Degree of destruction in % after 1 day |
| (A) | 0.1 | 100 |
| | 0.01 | 95 |
| | 0.001 | 0 |
| (2) | 0.1 | 100 |
| | 0.01 | 100 |
| | 0.001 | 100 |
| (1) | 0.1 | 100 |
| | 0.01 | 100 |
| | 0.001 | 100 |
| (3) | 0.1 | 100 |
| | 0.01 | 100 |
| | 0.001 | 100 |
| (5) | 0.1 | 100 |
| | 0.01 | 100 |
| | 0.001 | 100 |
| (4) | 0.1 | 100 |
| | 0.01 | 100 |
| | 0.001 | 100 |

EXAMPLE 3

Tetranychus test (resistant)

Solvent: 3 parts by weight of acetone

Emulsifier: 1 part by weight of alkylaryl polyglycol ether

To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% meant that all of the spider mites were killed whereas 0% meant that none of the spider mites were killed.

The active compounds, the concentrations of the active compounds, the evaluation times and the results can be seen from the following table:

TABLE 3

| | (mites which damage plants) *Tetranychus* Test | |
|---|---|---|
| Active compounds | Active compound concentration in % | Degree of destruction in % after 2 days |
| (A) | 0.1 | 98 |
| | 0.01 | 20 |
| (1) | 0.1 | 100 |
| | 0.01 | 98 |

It will be appreciated that the instant specification and examples are set forth by way of illustration and not limitation, and that various modifications and changes may be made without departing from the spirit and scope of the present invention.

What we claim is:

1. An O,O-dialkyl-O-[1-isopropyl-1,6-dihydro-6-oxo-pyridazin-3-yl]-phosphoric acid ester of the formula

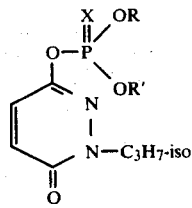

wherein
R and R' each independently is alkyl with 1 to 8 carbon atoms, and
X is oxygen or sulphur.

2. An ester according to claim 1,
wherein
R and R' each independently is alkyl with 1 to 4 carbon atoms, and
X is sulphur.

3. An ester according to claim 1, wherein such ester is O,O-diethyl-O-[1-isopropyl-1,6-dihydro-6-oxo-pyridazin-3-yl]-thionophosphoric acid ester of the formula

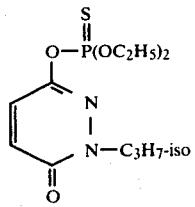

4. An ester according to claim 1, wherein such ester is O,O-dimethyl-O-[1-isopropyl-1,6-dihydro-6-oxo-pyridazin-3-yl]-thionophosphoric acid ester of the formula

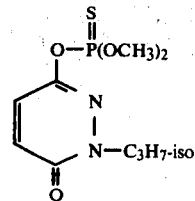

5. An ester according to claim 1, wherein such ester is O,O,-diethyl-O-[1-isopropyl-1,6-dihydro-6-oxo-pyridazin-3-yl]-phosphoric acid ester of the formula

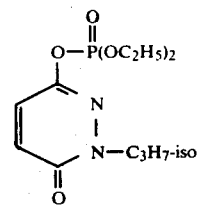

6. An ester according to claim 1, wherein such ester is O-methyl-O-n-propyl-O[1-isopropyl-1,6-dihydro-6-oxo-pyridazin-3-yl]-thionophosphoric acid ester of the formula

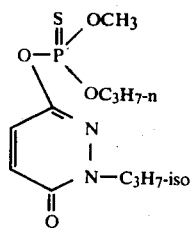

7. An ester according to claim 1, wherein such ester is O-ethyl-O-n-propyl-O-[1-isopropyl-1,6-dihydro-6-oxo-pyridazin-3-yl]-thionophosphoric acid ester of the formula

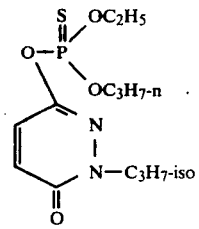

8. An insecticidal and acaricidal composition containing as active ingredient an insecticidal and acaricidal effective amount of an ester according to claim 1 in admixture with a diluent.

9. A method of combating insects and acarids which comprises applying to the insects and acarids, or to a habitat thereof, an insecticidally or acardicidally effective amount of an ester according to claim 1.

10. The method according to claim 9, in which said ester is O,O-diethyl-O-[1-isopropyl-1,6-dihydro-6-oxo-pyridazin-3-yl]-thionophosphoric acid ester, O,O-dimethyl-O-[1-isopropyl-1,6-dihydro-6-oxo-pyridazin-3-yl]-thionophosphoric acid ester, O,O-diethyl-O-[1-isopropyl-1,6-dihydro-6-oxo-pyridazin-3-yl]-phosphoric acid ester, O-methyl-O-n-propyl-O[1-isopropyl-1,6-dihydro-6-oxo-pyridazin-3-yl]-thionophosphoric acid ester, or O-ethyl-O-n-propyl-O-[1-isopropyl-1,6-dihydro-6-oxo-pyridazin-3-yl]-thionophosphoric acid ester.

* * * * *